United States Patent [19]

Ohtsuka et al.

[11] Patent Number: 5,665,120
[45] Date of Patent: Sep. 9, 1997

[54] BIOMEDICAL MATERIAL INCLUDING TUBE-LIKE BIODEGRADEABLE NETY WORKS FILLED WITH HYDROXYLAPATITE

[75] Inventors: Torao Ohtsuka; Makoto Fukaya, both of Aichi; Hideo Tagai, Tokyo; Shigeo Niwa, Aichi; Kazuhiko Sawai, Aichi; Hajime Ohta, Aichi, all of Japan

[73] Assignee: Tohkai Ceramic Material Co., Ltd., Japan

[21] Appl. No.: 596,914

[22] Filed: Mar. 15, 1996

Related U.S. Application Data

[63] Continuation of Ser. No. 210,635, Mar. 18, 1994, abandoned, which is a continuation of Ser. No. 868,947, Apr. 15, 1992, abandoned.

[30] Foreign Application Priority Data

Aug. 27, 1991 [JP] Japan ................................. 3-296693

[51] Int. Cl.⁶ .................................................. A61F 2/28
[52] U.S. Cl. ........................................................ 623/16
[58] Field of Search ....................... 623/16, 66; 424/422, 424/423, 424, 425, 426

[56] References Cited

U.S. PATENT DOCUMENTS

| | | | |
|---|---|---|---|
| 4,755,184 | 7/1988 | Silverberg | 623/16 |
| 4,839,215 | 6/1989 | Starling et al. | 428/131 |
| 5,034,352 | 7/1991 | Vit et al. | 623/16 |
| 5,266,248 | 11/1993 | Ohtsuka et al. | 623/16 |

Primary Examiner—Debra S. Brittingham
Attorney, Agent, or Firm—Ostrolenk, Faber, Gerb & Soffen, LLP

[57] ABSTRACT

A biomedical material in use for curing the bone defect or the like in human being or an animal. The biomedical material is comprised of a flexible fiber-meshed micro-tube which has an outer diameter ranging from 50 μm to 10 mm and is formed of a net or a cloth woven from fibers. The fibers are biodegradable and capable of maintaining their shape within a time period ranging from 1 week to 30 weeks in the body. Additionally, hydroxylapatite beads and/or flakes are filled in the fiber-meshed micro-tube. The biomedical material is located in the bone defect or the like under an operation, in which blood can effectively circulate through the mesh of the micro-tube and through the spaces among the hydroxylapatite beads and/or flakes, thereby promoting the cure of the bone defect or the like.

14 Claims, 3 Drawing Sheets

5μm

100μm

200μm

5μm

BIOMEDICAL MATERIAL INCLUDING TUBE-LIKE BIODEGRADEABLE NETY WORKS FILLED WITH HYDROXYLAPATITE

This application is a continuation of application Ser. No. 08/210,035, filed on 18 Mar. 1994, which was a continuation of application Ser. No. 07/868,947 filed on 15 Apr. 1992, both now abandoned.

BACKGROUND OF THE INVENTION

1. Field of the invention

This invention relates to improvements in a biomedical material for curing a bone defect or the like of human beings or animals, and more particularly to such a biomedical material including hydroxylapatite beads and/or flakes in order to make possible an early and nearly complete cure for the bone defect or the like.

2. Description of the Prior Art

Hitherto some biomedical materials for curing the bone defect or the like of human beings and animals have been proposed and put into practical use, as set forth below.

<First conventional technique>

Hydroxylapatite powder is fabricated into a variety of shapes and then fired to be solidified thereby to obtain a biomedical material applied to the bone defect of a variety of sizes and shapes. Otherwise, irregularly shaped hydroxylapatite power is mixed with a binder such as a biodegradable polymer or acid and then solidified to obtain a biomedical material.

<Second conventional technique>

Hydroxylapatite powder is mixed with the binder such as the biodegradable polymer or acid to form a hydroxylapatite paste as a biomedical material. The thus formed paste is flowable and therefore well fittable to a variety of shapes of bone defects.

However, drawbacks have been encountered in the above-discussed first and second conventional techniques, as set forth below. Concerning the first conventional technique, the biomedical material has been solidified to take a certain shape before use for curing the bone defect. Accordingly, even if a variety of shapes of such conventional biomedical materials are prepared, it is very difficult to effectively and uniformly disperse the biomedical material throughout, for example, an irregularly shaped bone defect or an irregular shaped space between the surface of a bone defect and an implant in case of cure using an implantation. As a result, according to this first conventional technique, a cure for the bone defect usually requires a time period of several months to more than 1 year.

Concerning the second conventional technique, this is advantageous and seems slightly advanced over the first conventional technique in a point at which the hydroxylapatite paste can be filled to be fittable to the irregularly shaped bone defect. However, since the biomedical material formed from the hydroxylapatite paste is not porous, it is small in specific surface area and insufficient in amount of circulation of blood through the biomedical material. As a result, bone conduction or new bone formation is obstructed or retarded not only in a deep portion of the biomedical material but also in a surface portion of the same. This lowers the inherent effect of bone formation of the biomedical material, so that a cure for the bone defect requires several months.

SUMMARY OF THE INVENTION

It is an object of the present invention to provide an improved biomedical material to be used for curing a bone defect or the like, which can overcome the drawbacks encountered in a variety of conventional similar biomedical materials.

Another object of the present invention is to provide an improved biomedical material to be used for curing a bone defect or the like, by which a time period required for the cure is largely shortened as compared with the similar conventional biomedical material so that the cure time period can be suppressed to only 2 to 3 weeks or shortened one third or fourth of that of the conventional biomedical materials.

A biomedical material of the present invention is comprised of a flexible meshed tube which has an outer diameter ranging from 50 μm to 10 mm and formed of a porous woven sheet. The porous woven sheet is formed of fibers which are biodegradable and capable of maintaining their shape within a time period ranging from 1 week to 30 weeks in an organism. Additionally, small subdivisions (beads and/or flakes) of hydroxylapatite are filled in the meshed tube.

Accordingly, after the biomedical material is implanted in the defect of bone, blood containing nutritive substances can freely circulate through the meshed tube and through spaces among the hydroxylapatite beads and/or flakes, thereby largely shortening the time period required for cure of the bone defect as compared with that required in the conventional techniques.

DETAILED DESCRIPTION OF THE INVENTION

Figure 1:
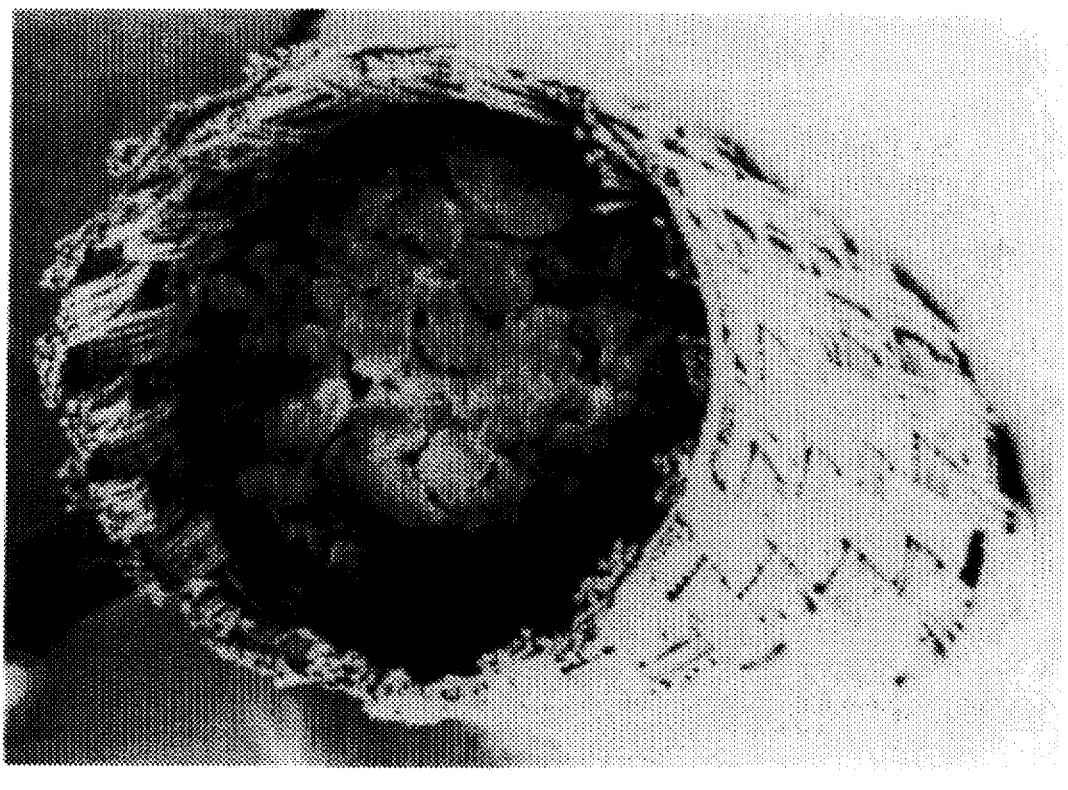
FIG. 1 is a scanning electron microphotograph (S. E. M) at about 150 magnifications of a biomedical material according to the present invention, showing a fiber-meshed micro-tube formed of polyglycolic acid base material with porous hydroxylapatite beads and flakes.

According to the present invention, there is provided a biomedical material comprised of a flexible fiber-meshed micro-tube which has an outer diameter ranging from 50 μm to 10 mm. The fiber-meshed micro-tube is formed of a porous woven sheet of fibers which are biodegradable and capable of maintaining their shape within a time period ranging from 1 week to 30 weeks in the body. Additionally, small subdivisions of hydroxylapatite are filled in the fiber-meshed micro-tube. Meant by the term "small subdivisions" are beads, flakes and/or other small and fine matters having a variety of shapes. In this case, the biomedical material is applied for curing a bone defect of human beings and animals.

The above-mentioned fibers forming the porous woven sheet are made of polyglycolic acid base or system material or polyglactine base or system material. Meant by the term "base" or "system" is the fact that the major component of the material is polyglycolic acid or poly-glycine. The polyglycine is sold under the trade name of "Poli-Glactin 910" and available from ETHICON Co., Ltd. Otherwise, the fibers are made of a mixture of the polyglycolic acid base material and the polyglycine base material. The fibers are biodegradable within a time period ranging from 1 week to 30 weeks in case that each of the fibers has a diameter ranging from 1 μm to 10 μm, which range may be slightly variable according to the kinds of the materials or to conditions to which the fibers are subjected. The fiber-meshed micro-tube may be closed at at least one of the opposite ends thereof thereby to be formed into a generally bag-shape. The porous woven sheet forming the fiber-meshed micro-tube is in the form of a net or a cloth, and available from NIPPON SHOJI Co., Ltd. in Japan.

It is necessary that the outer diameter of the fiber-meshed micro-tube is within a range of from 50 μm to 10 mm. If the outer diameter is larger than 10 mm, the biomedical material is difficult to be inserted into a defect of an animal body or a human body, or into an irregular space of the bone. Additionally, it will be understood that the size of mesh. (or each opening) of the fiber-meshed micro-tube is smaller than the diameter of the hydroxylapatite beads and/or flakes filled in the fiber-meshed micro-tube.

The hydroxylapatite beads and/or flakes are preferably porous. The hydroxylapatite beads and/or flakes may be not porous if it is bone-conductive and sufficiently fine. The hydroxylapatite beads and/or flakes are produced by firing green (not yet fired) hydroxylapatite beads and/or flakes at a temperature ranging from 750° C. to 1150° C. This is because the rate of fired beads and/or flakes is less if firing is made at a temperature lower than 750° C., whereas the rate of molten beads and/or flakes increases thereby to make the beads and/or flakes too inactive if the firing is made at a temperature higher than 1150° C. It is preferable that the diameter of the hydroxylapatite beads and/or flakes is within a range of from 0.2 μm to 300 μm. This is because a particle size control for the beads and/or flakes is difficult if the diameter is less than 0.2 μm, whereas a space or gap between the adjacent beads and/or flakes becomes too large thereby to reduce the curing effect of the biomedical material if the diameter exceeds 300 μm. It will be understood that each of the hydroxylapatite beads are usually generally spherical; however, the hydroxylapatite flakes or the likes may not be generally spherical. In case of being not generally spherical, the "diameter" of the flake or the like represents an average of the lengths of the minor and major axes of the flake or the like. The hydroxylapatite beads and/or flakes (not porous) are available from MITSUBISHI MATERIAL Co., Ltd. in Japan.

It is preferable that each porous hydroxylapatite bead and/or flake has a plurality of pores each having a diameter ranging from 1 to 100 μm and a length larger than the pore diameter, and each bead and/or flake has a porosity (the rate in volume of the pore relative to the bead and/or flake) ranging from 10 to 50%. It is also preferable that the porous hydroxylapatite beads and/or flakes are produced by the following method: First, hydroxylapatite powder (having particle sizes not larger than 125 μm and in an amount ranging from 40 to 90% by weight) is mixed with synthetic resin powder (having particle sizes not larger than 74 and in an amount ranging from 5 to 55% by weight), and resinous binder (in an amount ranging from 0.5 to 5% by weight) to obtain a mixture. Then, the mixture is granulated to form beads and/or flakes each having a diameter ranging from 0.2 to 300 μm. Finally, the beads and/or flakes are fired at a temperature ranging from 750° C. to 1150° C.

The advantageous effect of the biomedical material according to the present invention will be discussed hereinafter.

The biomedical material of the present invention can overcome nearly all the drawbacks encountered in and be largely improved over the first and second conventional techniques using the similar biomedical material. That is to say, the fiber-meshed micro-tube filled with the hydroxylapatite beads and/or flakes is flexible and soft, and therefore the biomedical material of the present invention can be effectively fittably filled into an irregularly shaped defect of the bone or the like, hardly forming a space between the surface of the bone defect. In contrast, according to the above-discussed first conventional technique, even if a variety of shapes and sizes of the biomedical materials or fired products are prepared, it is difficult to cause the fired product to effectively fit in shape to the irregularly shaped bone defect.

Additionally, according to the biomedical material of the present invention, blood can freely circulate through the fiber-meshed micro-tube formed of the woven net or cloth, and also through the spaces among the hydroxylapatite beads and/or flakes filled in the the fiber-meshed micro-tube. In case that each hydroxylapatite bead and/or flake is porous, blood flows through the pores of each hydroxylapatite bead and/or flake, so that such blood circulation is further improved. The thus improved blood flow through the biomedical material and the bone defect effectively promotes the osteoconduction or new bone formation, causing the hydroxylapatite beads and/or flakes to effectively exhibit a biocompatibility with the bone. Thus, the biomedical material of the present invention exhibits a high bone conductivity, thereby largely shortening a time period required for the cure of the bone defect or the like as compared with even the above-discussed second conventional technique. In this connection, according to the second conventional technique, the hydroxylapatite biomedical material is not porous and therefore small in specific surface area. Accordingly, when the hydroxylapatite biomedical material is filled in the bone defect, the blood of the organism cannot flow through the biomedical material so that blood cannot sufficiently circulate through a cure-required part or the bone defect, so that a long time is required for the cure.

EXAMPLE 1

This experiment was conducted using the biomedical material including the net-shaped fiber-meshed micro-tube filled with usual available hydroxylapatite beads and flakes (referred hereinafter to as "HAP"). The fiber-meshed micro-tube had been prepared by weaving polyglycolic acid (referred hereinafter to as "PGA") base filaments or fibers each having a diameter of about 10 μm. The fiber-meshed micro-tube had an outer diameter of 1.00 mm and an inner diameter of 0.87 mm. The hydroxylapatite beads and flakes filled in the fiber-meshed micro-tube had been prepared upon firing green hydroxylapatite beads and flakes at 900° C. and had a diameter ranging from 100 μm to 200 μm.

The biomedical material was implanted in a hole formed through a femoral condyle of each of eight rabbits which had weights of 3 kg to 4 kg. These rabbits were sacrificed at a time of 2, 4 and 6 weeks after the implantation of the biomedical material in the rabbit's femoral condyle, and then a non-decalcified sample of the tissue of each rabbit was produced according to a Hematoxylin and Eosin staining method. The non-decalcified sample was subjected to a microscopic observation in which osteanagenesis or new bone formation was observed. Additionally, the non-calcified sample was subjected to a quantitative analysis of a newly formed bone for the samples which were generally equal in an occupying rate of HAP by using an image analysis system.

The quantitative analysis of the newly formed bone was carried out as follows: First, an inscribed circle of the inner surface of the fiber-meshed micro-tube was described on a cross-sectional image of the elongate biomedical material thereby to form a measuring-objective circular region. Then, a calculation was made to obtain a ratio of the area of the newly formed bone relative to an initial empty area which was an area obtained by subtracting HAP from the whole measuring-objective circular region. As a result of the above experiments, no foreign body or no rejective reactions were recognized by the microscopic observation. Additionally, it was recognized by the newly formed bone determination, that a considerable new bone tissue was formed at a time of four weeks after the implantation, in which the ratio of the newly formed bone relative to the initial empty area reached about 60%. At six weeks after the operation, the ratio of the newly formed bone increased to about 64%. This demonstrated that only 1.5 to 2 months were required for the cure of a bone defect though several months or longer were required for the same cure in the conventional techniques.

EXAMPLE 2

Figure 2:
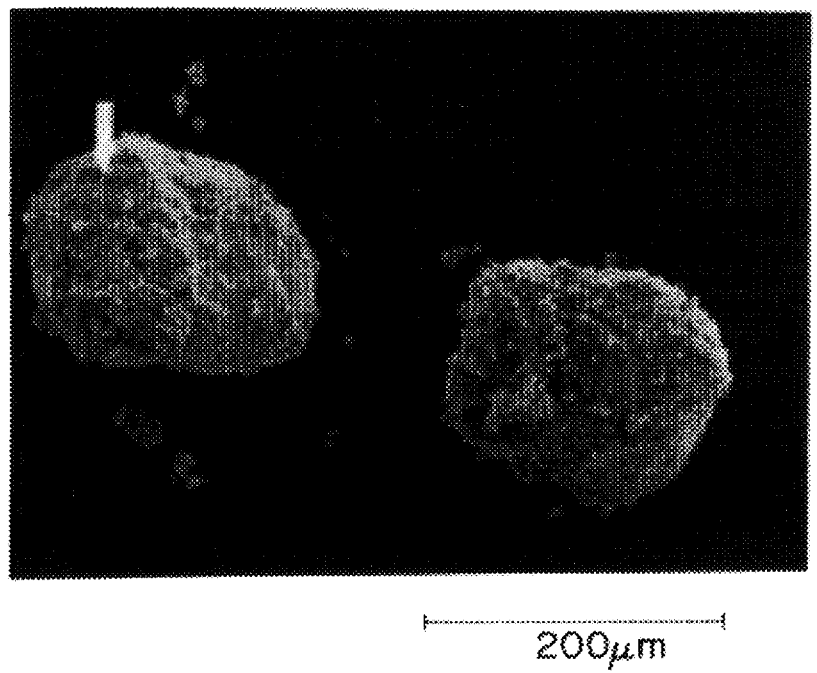
FIG. 2 is a S. E. M. at about 200 magnifications of the porous hydroxylapatite beads and flakes shown in FIG. 1.
Figure 3:
FIG. 3 is a S. E. M. at about 10 thousand magnification, showing the porous microstructure of the porous hydroxylapatite beads and flakes, at a location indicated by the tip end of a bright arrow in FIG. 2.

This experiment was conducted similarly to that in EXAMPLE 1 with the exception that the used biomedical material includes the net-shaped fiber-meshed micro-tube filled with porous hydroxylapatite beads and flakes. The procedure of the experiment was generally the same as that in EXAMPLE 1, in which scanning electron microphotograph (S. E. M.) of the biomedical material were taken as shown in FIGS. 1 to 3. FIG. 1 shows the fiber-meshed micro-tube of polyglycolic acid (PGA) base fibers, filled with the porous hydroxylapatite beads and flakes. FIG. 2 is a further enlarged photograph of FIG. 1 and shows the porous hydroxylapatite beads and flakes having diameters ranging from 100 μm to 200 μm. FIG. 3 is a further enlarged photograph over FIG. 2 and indicates a porous structure formed of fine particles, at a location indicated by the tip end of a bright arrow shown in FIG. 2.

In the experiment, the biomedical material was implanted in the hole formed through the portion of the femoral condyle of each of the rabbits. Upon lapse of 2 weeks and 4 weeks after the implantation, the tissue of the embedded biomedical material was sampled, upon which the non-decalcified sample for each tissue was produced according to the Hematoxylin and Eosin staining method. The non-decalcified sample was subjected to the microscopic observation using a microscope and the determination of the newly formed bone using the computer image analysis system.

According to the microscopic observation, the followings were recognized: No foreign body reaction was made. Upon lapse of 2 weeks after the implantation, a large amount of new bone tissue was formed inside the fiber-meshed micro-tube, and further new bone tissue was formed through the mesh of the net-shaped fiber-meshed micro-tube and extends from the inside to the outside of the fiber-meshed micro-tube. Upon lapse of 4 weeks after the implantation, the amount of the bone tissue extending from the inside to the outside of the fiber-meshed micro-tube further increased.

The determination of the newly formed bone demonstrated that the ratio of the newly formed bone relative to the initial empty area reached about 65% at a time of 2 weeks after the implantation and increased to about 69% at a time of 4 weeks after the implantation.

The above experiment was repeated under a condition in which the fiber-meshed micro-tube was formed of polyglacin base or system fibers in place of the polyglycolic acid base fibers. As a result, nearly the same results were obtained.

The above experiments have revealed that the advantageous effects of the biomedical material of the present invention were greatly improved by using the porous hydroxylapatite beads and flakes to be filled in the fiber-meshed micro-tube.

What is claimed is:

1. A biomedical material comprising:
   a flexible meshed tube having an outer diameter ranging from 50 mm to 10 mm and formed of a porous woven sheet of fibers having a particular shape which are biodegradable and capable of maintaining their shape within a time period ranging from 1 week to 30 weeks in an organism; and
   porous hydroxylapatite beads loosely filled in said meshed tube to permit free circulation of blood through the meshed tube and between said porous hydroxylapatite beads to promote osteoconduction, each of said porous hydroxylapatite beads having a plurality of pores connected to one another to form a network, each of said pores having a diameter ranging from 1 to 10 mm and a length larger than the pore diameter, each of said porous hydroxylapatite beads having a porosity ranging from 10 to 50%.

2. A biomedical material as claimed in claim 1, wherein said small subdivisions of hydroxylapatite are hydroxylapatite beads.

3. A biomedical material as claimed in claim 2, wherein said small subdivisions of hydroxylapatite are hydroxylapatite flakes.

4. A biomedical material as claimed in claim 1, wherein at least one of opposite ends of said meshed tube is closed so as to be bag-shaped.

5. A biomedical material as claimed in claim 1, wherein said porous woven sheet is a net.

6. A biomedical material as claimed in claim 1, wherein said porous woven sheet is a cloth.

7. A biomedical material as claimed in claim 1, wherein said fibers are polyglycolic acid base material.

8. A biomedical material as claimed in claim 1, wherein fibers are polyglycine base material.

9. A biomedical material as claimed in claim 1, wherein a size of mesh of said porous woven sheet is smaller than a diameter of said small subdivisions of hydroxylapatite.

10. A biomedical material as claimed in claim 1, wherein a diameter of each of said small subdivisions of hydroxylapatite is within 0.2 μm to 300 μm.

11. A biomedical material as claimed in claim 1, wherein said small subdivisions of hydroxylapatite are produced upon being fired at a temperature within a range from 750° C. to 1150° C.

12. A biomedical material as claimed in claim 1, wherein each of said fibers has a diameter ranging from 1 μm to 10 μm.

13. A biomedical material as claimed in claim 1, wherein said biomedical material is used to be filled in a bone defect in a manner to contact with the surface of the bone defect.

14. A biomedical material comprising:
   a flexible meshed tube having an outer diameter ranging from 50 mm to 10 mm and formed of a porous woven sheet of fibers having a particular shape which are biodegradable and capable of maintaining their shape within a time period ranging from 1 week to 30 weeks in an organism; and
   porous hydroxylapatite beads loosely filled in said meshed tube to permit free circulation of blood through the meshed tube and between said porous hydroxylapatite beads to promote osteoconduction, each of said porous hydroxylapatite beads having a plurality of pores connected to one another to form a network, each of said pores having a diameter ranging from 1 to 10 mm and a length larger than the pore diameter, each of said porous hydroxylapatite beads having a porosity ranging from 10 to 50%, said porous hydroxylapatite beads being produced by mixing hydroxylapatite powder having particle sizes not larger than 125 mm and in an amount ranging from 40 to 90% by weight with synthetic resin powder having particle sizes not larger than 74 mm and in an amount ranging from 5 to 55% by weight, and resinous binder in an amount ranging from 0.5 to 5% by weight to obtain a mixture; granulating said mixture to form beads each having a diameter ranging from 0.2 to 300 um; and firing said beads at a temperature ranging from 750° C. to 1150° C.

* * * * *